United States Patent
Huang et al.

(10) Patent No.: US 12,048,808 B2
(45) Date of Patent: Jul. 30, 2024

(54) ANESTHESIA MACHINE AND VENTILATION STATE INDICATION SYSTEM THEREOF

(71) Applicants: SHENZHEN MINDRAY BIO-MEDICAL ELECTRONICS CO., LTD., Shenzhen (CN); SHENZHEN MINDRAY SCIENTIFIC CO., LTD., Shenzhen (CN)

(72) Inventors: Chenghua Huang, Shenzhen (CN); Ruiling Pan, Shenzhen (CN); Huihua Wang, Shenzhen (CN)

(73) Assignees: SHENZHEN MINDRAY BIO-MEDICAL ELECTRONICS CO., LTD., Shenzhen (CN); SHENZHEN MINDRAY SCIENTIFIC CO., LTD., Shenzhen (CN)

( * ) Notice: Subject to any disclaimer, the term of this patent is extended or adjusted under 35 U.S.C. 154(b) by 1137 days.

(21) Appl. No.: 16/757,367

(22) PCT Filed: Oct. 20, 2017

(86) PCT No.: PCT/CN2017/107096
§ 371 (c)(1),
(2) Date: Jun. 21, 2020

(87) PCT Pub. No.: WO2019/075744
PCT Pub. Date: Apr. 25, 2019

(65) Prior Publication Data
US 2020/0306471 A1 Oct. 1, 2020

(51) Int. Cl.
*A61M 16/00* (2006.01)
*A61M 16/01* (2006.01)

(52) U.S. Cl.
CPC ........ *A61M 16/01* (2013.01); *A61M 16/0003* (2014.02); *A61M 2016/0039* (2013.01);
(Continued)

(58) Field of Classification Search
CPC .............. A61M 16/01; A61M 16/0003; A61M 2016/0039; A61M 2016/0042; A61M 2205/18; A61M 2205/502
See application file for complete search history.

(56) References Cited

U.S. PATENT DOCUMENTS

2007/0199566 A1   8/2007   Eliezer
2012/0180793 A1   7/2012   Schoepke
(Continued)

FOREIGN PATENT DOCUMENTS

CN   1610516 A     4/2005
CN   103080942 A   5/2013
(Continued)

OTHER PUBLICATIONS

First Office Action issued in related Chinese Application No. 201780095964.0, mailed May 31, 2022, 9 pages.
(Continued)

*Primary Examiner* — Steven O Douglas
(74) *Attorney, Agent, or Firm* — BAYES PLLC

(57) ABSTRACT

An anesthesia machine ventilation state indication system, used for indicating the ventilation state of an anesthesia machine. The anesthesia machine ventilation state indication system includes an electronic display interface including one ventilation state indicating graphic; a parameter acquiring module used for acquiring a ventilation parameter; and a control module used for obtaining a change in the volume of a driving gas and a change in the volume of a gas in the patient circuit according to the ventilation parameter acquired, and employing the ventilation state indicating
(Continued)

graphic to dynamically display at the same time the change in the volume of the driving gas and the change in the volume of the gas in the patient circuit on the electronic display interface.

20 Claims, 8 Drawing Sheets

(52) U.S. Cl.
CPC . *A61M 2016/0042* (2013.01); *A61M 2205/18* (2013.01); *A61M 2205/502* (2013.01)

(56) References Cited

U.S. PATENT DOCUMENTS

| | | |
|---|---|---|
| 2015/0250960 A1 | 9/2015 | Broberg et al. |
| 2016/0035122 A1 | 2/2016 | Stewart et al. |

FOREIGN PATENT DOCUMENTS

| | | |
|---|---|---|
| CN | 103520814 A | 1/2014 |
| CN | 104619371 A | 5/2015 |
| EP | 2682147 A2 | 1/2014 |
| WO | 2012083276 A2 | 6/2012 |
| WO | 2017001561 A1 | 1/2017 |

OTHER PUBLICATIONS

Extended European Search Report issued in related European Application No. 17928969.9, mailed Sep. 3, 2020, 7 pages.
Second Office Action issued in related Chinese Application No. 201780095964.0, mailed Dec. 21, 2022, 6 pages.
International Search Report issued in corresponding International Application No. PCT/CN2017/107096, mailed Jul. 27, 2018, 4 pages.

ANESTHESIA MACHINE AND VENTILATION STATE INDICATION SYSTEM THEREOF

CROSS-REFERENCE TO RELATED APPLICATIONS

This application is a U.S. national phase application of PCT Application No. PCT/CN2017/107096, filed Oct. 20, 2017, entitled "ANESTHESIA MACHINE AND VENTILATION STATE INDICATION SYSTEM THEREOF," the entire contents of which are incorporated herein by reference.

TECHNICAL FIELD

This disclosure relates to the technical field of anesthesia machines, and in particular to an anesthesia machine and a ventilation state indication system thereof.

BACKGROUND ART

An anesthesia machine is an apparatus that enables inhalation anesthesia and mechanical ventilation for a patient during surgery. The anesthesia machine provides mechanical ventilation support for the patient to keep airway unobstructed, improve the ventilation and oxygenation, and prevent the body from hypoxia and $CO_2$ accumulation. During surgery, the abnormal stop of mechanical ventilation or the abnormal gas supply of the machine may, if it is not detected in time, cause the patient to suffocate for a long time, which will directly affect the patient's safety.

In order to facilitate the relevant personnel to know the ventilation state of the anesthesia machine in time, in the prior art, the ventilation state of the anesthesia machine is indicated by the motion of a bellows. The bellows is marked with a scale, and the tidal volume of gas supply can be directly read from the scale. If a ventilator malfunctions, the bellows will stop, and in the case of patient disconnection or serious leakage, the bellows will collapse. This method can directly reflect the working state of the anesthesia machine, but it needs to rely on the bellows that is a relatively complex hardware device, so there are some obvious problems, for example, the bellows drive cannot achieve 0 PEEP ventilation. A user sets PEEP to 0, but a monitoring value may be 2 or 3. The bellows is a moving part and needs to be maintained or replaced regularly, and thus the use cost is high. Because a driving gas of the bellows is isolated from the patient, the user needs to remove the bellows when calibrating a sensor, which is troublesome. The bellows design itself may cause leakage of the system. For anesthesia machines that do not use a bellows to isolate a driving gas from a patient circuit gas, the ventilation state cannot be indicated.

In summary, it can be seen that how to intuitively indicate the ventilation state of the anesthesia machine is an urgent problem to be solved at present.

SUMMARY OF THE DISCLOSURE

In view of this, an object of this disclosure is to provide an anesthesia machine and a ventilation state indication system thereof for the purpose of indicating the ventilation state of the anesthesia machine more intuitively. The specific solution thereof is as follows: an anesthesia machine ventilation state indication system, may be used for indicating the ventilation state of an anesthesia machine, the system may include: an electronic display interface may include one ventilation state indicating graphic; a parameter acquiring module may be used for acquiring a ventilation parameter; and a control module may be used for obtaining a change in the volume of a driving gas and a change in the volume of a gas in the patient circuit according to the ventilation parameter acquired, and employing the ventilation state indicating graphic to dynamically display at the same time the change in the volume of the driving gas and the change in the volume of the gas in the patient circuit on the electronic display interface.

In one embodiment, the parameter acquiring module may include an expiratory flow sensor may be used for acquiring an expiratory flow, and an inspiratory flow sensor may be used for acquiring an inspiratory flow and/or a driving gas flow sensor may be used for acquiring a driving gas flow; and the control module may be used for calculating to obtain the change in the volume of the gas in the patient circuit according to the expiratory flow acquired, and calculating to obtain the change in the volume of the driving gas according to the inspiratory flow or the driving gas flow acquired.

In one embodiment, the ventilation state indicating graphic may be an indicating graphic of a non-bar structure.

In one embodiment, the ventilation state indicating graphic may include a section for displaying a state of a driving gas and a section for displaying a state of a gas in the patient circuit.

In one embodiment, the control module may be used for respectively controlling the change in indication attributes of the section for displaying a state of a driving gas and the section for displaying a state of a gas in the patient circuit according to the change in the volume of the driving gas and the change in the volume of the gas in the patient circuit; wherein the indication attributes may include one or more of length, width, area, thickness, volume, color saturation, or display brightness.

In one embodiment, the control module may be further used for, when abnormal ventilation is detected, indicating corresponding abnormal ventilation information on the ventilation state indicating graphic.

In one embodiment, the abnormal ventilation may include one or more of ventilation failure of the anesthesia machine, patient disconnection, or insufficient gas supply of the anesthesia machine.

In one embodiment, the abnormal ventilation may be indicated by one or more of the indication attribute of the section for displaying a state of a driving gas, the indication attribute of the section for displaying a state of a gas in the patient circuit, or multimedia information.

In one embodiment, the multimedia information may include one or more of an icon, a color, a text, or a sound used for indicating the abnormal ventilation.

In one embodiment, the electronic display interface further may include a lung graphic, through which the control module may indicate the change in the volume of the gas in the patient circuit.

In one embodiment, the control module may be used for indicating the change in the volume of the gas in the patient circuit according to the change in a graphic parameter of the lung graphic and/or the change in an internal fill graphic of the lung graphic; wherein the graphic parameter may include one or more of size, color, or brightness of the lung graph.

In one embodiment, the control module may be further used for, when abnormal ventilation is detected, indicating corresponding abnormal ventilation information on the lung graphic.

Accordingly, this disclosure further discloses an anesthesia machine including the anesthesia machine ventilation state indication system disclosed above, the anesthesia machine further may include a driving gas branch, a bellows-free gas exchanger, a patient circuit and a fresh gas branch.

It can be seen that the electronic display interface of this disclosure may include one ventilation state indicating graphic. When the ventilation state of the anesthesia machine is indicated, the ventilation parameter may be firstly acquired by the parameter acquiring module, then the change in the volume of the driving gas and the change in the volume of the gas in the patient circuit may be obtained according to the ventilation parameter acquired, and then the change in the volume of the driving gas and the change in the volume of the gas in the patient circuit may be dynamically displayed at the same time on the electronic display interface through the ventilation state indicating graphic. That is, according to this disclosure, the change in the volume of the driving gas and the change in the volume of the gas in the patient circuit may be obtained by acquiring and processing the ventilation parameter, and then the change in the volume of the driving gas and the change in the volume of the gas in the patient circuit may be dynamically displayed through a carrier, i.e., an electronic graphic, so that the ventilation state of the anesthesia machine is indicated, and the ventilation state of the anesthesia machine can be displayed to the user more intuitively.

BRIEF DESCRIPTION OF THE DRAWINGS

In order to illustrate the technical solutions in the embodiments of this disclosure or in the prior art more clearly, a brief introduction to the figures to be used in the description of the embodiments or the prior art will be provided below. Obviously, the drawings in the following description show merely the embodiments of this disclosure, and those of ordinary skill in the art would have derived other drawings from the provided drawings without involving any inventive effort.

DETAILED DESCRIPTION OF EMBODIMENTS

The technical solutions of the embodiments of this disclosure will be described below clearly and comprehensively in conjunction with the drawings of the embodiments of this disclosure. Clearly, the embodiments described are merely some embodiments of this disclosure and are not all the possible embodiments. Based on the embodiments of this disclosure, all other embodiments obtained by those of ordinary skill in the art without involving any inventive effort fall within the scope of protection of this disclosure.

Figure 1:
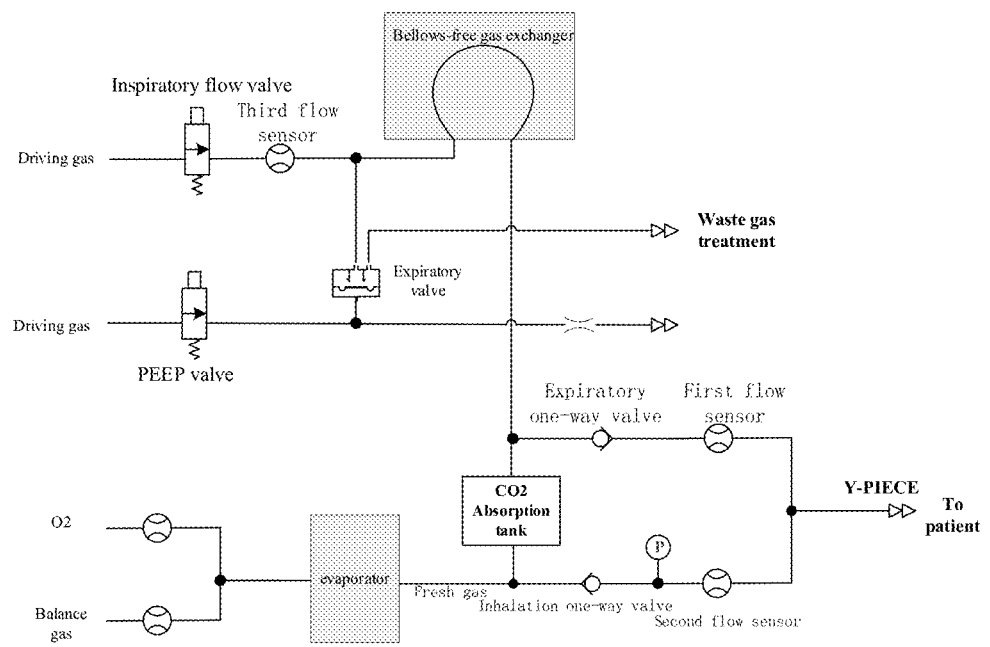
FIG. 1 is a gas path structural diagram of an anesthesia machine.

The technical solution disclosed in this disclosure may be applied to an anesthesia machine. FIG. 1 shows a specific gas path structural diagram of an anesthesia machine. The anesthesia machine may include a driving gas branch providing a driving gas, a bellows-free gas exchanger for isolating the driving gas from a gas in the patient circuit, a fresh gas branch providing a fresh gas, and a patient circuit connecting with the bellows-free gas exchanger, the fresh gas branch and a patient. In FIG. 1, the fresh gas with anesthetic delivered from an evaporator and the gas flowing out of a $CO_2$ absorption tank may enter the body of a patient through an inhalation branch, an exhaled gas from the patient flows into the bellows-free gas exchanger through an exhalation branch, and the excess gas may be discharged to the outside. In FIG. 1, the exhalation branch may be provided with an exhalation one-way valve and an expiratory flow sensor, and when the patient is exhaling gas, the corresponding expiratory flow can be acquired by the above expiratory flow sensor; and the inhalation branch may be provided with an inhalation one-way valve and an inspiratory flow sensor, and when the patient is inhaling gas, the corresponding inspiratory flow can be acquired by the above inspiratory flow sensor. In addition, in FIG. 1, a driving gas flow sensor may be further provided, and when the patient is inhaling gas, a driving gas flow can be acquired by the above driving gas flow sensor.

It should be noted that the bellows-free gas exchanger in FIG. 1 may be a device, different from a bellows, for isolating the driving gas from the gas in the patient circuit. Here, the above bellows-free gas exchanger may be specifically a volume reflector or a gas storage bag, etc.

Figure 2:
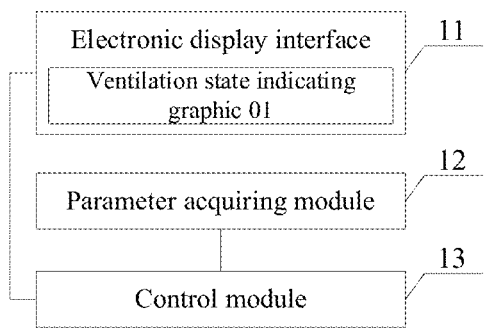
FIG. 2 is a structural diagram of a ventilation state indication system of an anesthesia machine disclosed in an embodiment of this disclosure.

As shown in FIG. 2, an embodiment of this disclosure discloses an anesthesia machine ventilation state indication system, used for indicating the ventilation state of an anesthesia machine, the system may include: an electronic display interface 11 may include one ventilation state indicating graphic 01; a parameter acquiring module 12 may be used for acquiring a ventilation parameter; and a control module 13 may be used for obtaining a change in the volume of the driving gas and a change in the volume of the gas in the patient circuit according to the ventilation parameter acquired by the parameter acquiring module 12, and employing the ventilation state indicating graphic 01 to dynamically display at the same time the change in the volume of the driving gas and the change in the volume of the gas in the patient circuit on the electronic display interface 11.

In one embodiment, the electronic display interface 11 may include one ventilation state indicating graphic 01. The shape and structure of the ventilation state indicating graphic 01 can be determined according to the actual application needs, as long as it can serve as a carrier that can dynamically display the changes in the volume of the driving gas and the volume of the gas in the patient circuit.

Figure 3:
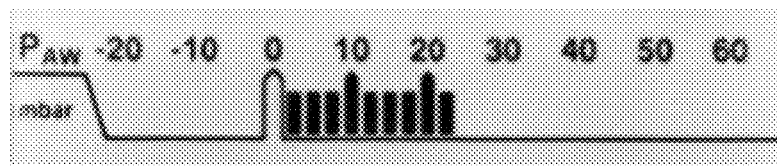
FIG. 3 is a specific ventilation state indicating diagram based on a pressure bar in the prior art.
Figure 4:
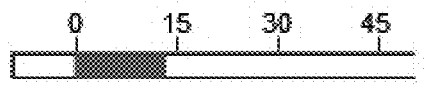
FIG. 4 is another specific ventilation state indicating diagram based on a pressure bar in the prior art.

Considering that the graphic of a bar structure as shown in FIG. 3 or 4 can only indicate information in transverse or longitudinal directions, resulting in a limited information indication range and being inconvenient for a user to clearly observe the ventilation state, in the embodiment of this disclosure, it is preferable to set the above ventilation state indicating graphic as an indicating graphic of a non-bar structure, and the boundary line thereof may be a curve or multiple segments of straight line, and may also include at the same time a curve and a straight line, such as a ring-like graphic, a polygonal graphic, a U-like graphic or a special-shaped graphic. It should be noted that the special-shaped graphic refers to a graphic with an irregular shape.

In addition, the ventilation state indicating graphic in one embodiment may be not merely limited to a two-dimensional planar indicating graphic, and may also be a three-dimensional indicating graphic.

It should be noted that the parameter acquiring module 12 in one embodiment can specifically acquire the ventilation parameter of the anesthesia machine by means of the flow sensor and transfer the ventilation parameter acquired to the control module 13, so that the control module 13 may determine the change in the volume of the driving gas and the change in the volume of the gas in the patient circuit according to the ventilation parameter acquired by the parameter acquiring module 12, and employ the ventilation state indicating graphic 01 to dynamically display at the same time the change in the volume of the driving gas and the change in the volume of the gas in the patient circuit on the electronic display interface 11, so that by means of observing the ventilation state indicating graphic 01 on the electronic display interface 11, the user can clearly know the change in the volume of the driving gas and the change in the volume of the gas in the patient circuit of the current anesthesia machine.

In one embodiment, when the patient is in an exhalation state, the control module 13 can determine the change in the volume of the gas in the patient circuit according to the current corresponding ventilation parameter to obtain the change in the volume of the driving gas.

In one embodiment, when the patient is in an inhalation state, the control module 13 can determine the change in the volume of the driving gas according to the current corresponding ventilation parameter to obtain the change in the volume of the gas in the patient circuit.

It can be seen from the above that in the embodiment of this disclosure, the change in the volume of the driving gas and the change in the volume of the gas in the patient circuit may be obtained by acquiring and processing the ventilation parameter, and then the change in the volume of the driving gas and the change in the volume of the gas in the patient circuit may be dynamically displayed through a carrier, i.e., an electronic graphic, so that the ventilation state of the anesthesia machine is indicated. Moreover, no bellows may be required in the above process, thereby avoiding problems such as poor reliability, high cost, and troublesome use caused by a bellows itself.

Figure 5:
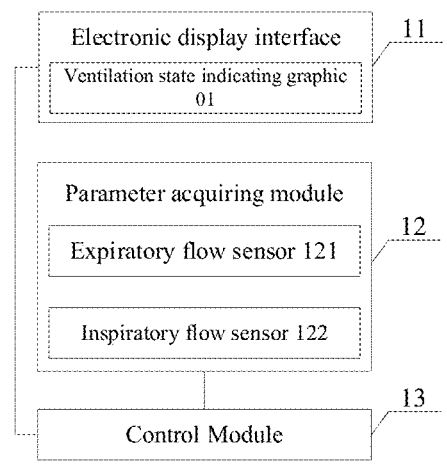
FIG. 5 is a structural diagram of a specific ventilation state indication system of an anesthesia machine disclosed in an embodiment of this disclosure.

According to the foregoing embodiment, as shown in FIG. 5, an embodiment of this disclosure discloses a specific anesthesia machine ventilation state indication system, may include: an electronic display interface 11 may include one ventilation state indicating graphic 01; a parameter acquiring module 12 may include an expiratory flow sensor 121 may be used for acquiring an expiratory flow, and an inspiratory flow sensor 122 may be used for acquiring an inspiratory flow; and a control module 13 may be used for calculating to obtain the change in the volume of the gas in the patient circuit according to the expiratory flow acquired by the expiratory flow sensor 121, calculating to obtain the change in the volume of the driving gas according to the inspiratory flow acquired by the inspiratory flow sensor 122, and employing a ventilation state indicating graphic 01 to dynamically display at the same time the change in the volume of the driving gas and the change in the volume of the gas in the patient circuit on the electronic display interface 11.

It can be understood that the expiratory flow sensor 121 in one embodiment may be a first flow sensor on the exhalation branch and can monitor the flow of the exhaled gas of the patient. Similarly, the inspiratory flow sensor 122 may be a second flow sensor on the inhalation branch, and can monitor the flow of the inhaled gas of the patient.

In one embodiment, when the patient is exhaling, the control module 13 may calculate to obtain the change in the volume of the gas in the patient circuit according to the expiratory flow acquired by the expiratory flow sensor 121, and can further deduce the change in the volume of the driving gas according to the change in the volume of the gas in the patient circuit.

In one embodiment, when the patient is inhaling, the control module 13 may calculate to obtain the change in the volume of the driving gas according to the inspiratory flow acquired by the inspiratory flow sensor 122, and can further deduce the change in the volume of the gas in the patient circuit according to the change in the volume of the driving gas.

Of course, in order to further improve the calculation accuracy of the change in the volume of the driving gas, the control module 13 in one embodiment can also calculate to obtain the change in the volume of the driving gas according to the inspiratory flow and the driving gas flow at the same time, which means that a driving gas flow sensor for acquiring a driving gas flow needs to be additionally provided in the above parameter acquiring module 12.

Figure 6:
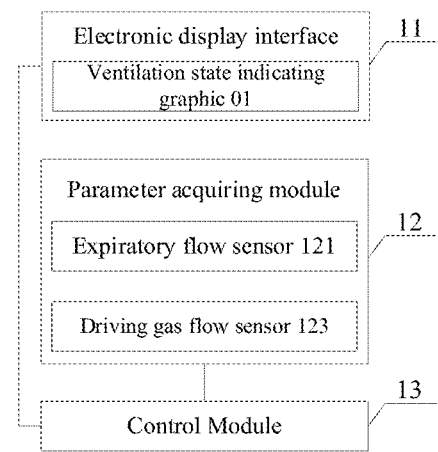
FIG. 6 is a structural diagram of a specific ventilation state indication system of an anesthesia machine disclosed in an embodiment of this disclosure.

As shown in FIG. 6, an embodiment of this disclosure discloses another specific anesthesia machine ventilation state indication system, may include: an electronic display interface 11 may include one ventilation state indicating graphic 01; a parameter acquiring module 12 may include an expiratory flow sensor 121 may be used for acquiring an expiratory flow, and a driving gas flow sensor 123 may be used for acquiring a driving gas flow; and a control module 13 may be used for calculating to obtain the change in the volume of the gas in the patient circuit according to the expiratory flow acquired, calculating to obtain the change in the volume of the driving gas according to the driving gas flow acquired, and employing a ventilation state indicating graphic 01 to dynamically display at the same time the change in the volume of the driving gas and the change in the volume of the gas in the patient circuit on the electronic display interface 11.

It can be understood that the expiratory flow sensor 121 in one embodiment may be a first flow sensor on the exhalation branch and can monitor the flow of the exhaled gas of the patient. Similarly, the driving gas flow sensor 123 may be a third flow sensor on the side where a driving gas source is located, and can monitor the flow of the driving gas.

In one embodiment, when the patient is exhaling, the control module 13 may be calculates to obtain the change in the volume of the gas in the patient circuit according to the expiratory flow acquired by the expiratory flow sensor 121, and can further deduce the change in the volume of the driving gas according to the change in the volume of the gas in the patient circuit.

In one embodiment, when the patient is inhaling, the control module 13 may be calculates to obtain the change in the volume of the driving gas according to the driving gas flow acquired by the driving gas flow sensor 123, and can further deduce the change in the volume of the gas in the patient circuit according to the change in the volume of the driving gas.

Of course, in order to further improve the calculation accuracy of the change in the volume of the driving gas, the control module 13 in one embodiment can also calculate to obtain the change in the volume of the driving gas according to the inspiratory flow and the driving gas flow at the same time, which means that an inspiratory flow sensor for acquiring an inspiratory flow needs to be additionally provided in the above parameter acquiring module 12.

According to each of the foregoing embodiments, the related technical solutions are further illustrated and optimized in the embodiments of this disclosure. Specifically, in one embodiment, the ventilation state indicating graphic in the electronic display interface can specifically include a section for displaying a state of a driving gas and a section for displaying a state of a gas in the patient circuit. It can be understood that the above section for displaying the state of the driving gas is a portion, in the ventilation state indicating graphic, may be used for displaying the change in the volume of the driving gas; and similarly, the above section for displaying the state of the gas in the patient circuit may be a portion, in the ventilation state indicating graphic, may be used for displaying the change in the volume of the gas in the patient circuit.

Accordingly, the control module in one embodiment can be specifically used for respectively controlling the change in indication attributes of the section for displaying the state of the driving gas and the section for displaying the state of the gas in the patient circuit according to the change in the volume of the driving gas and the change in the volume of the gas in the patient circuit; wherein the indication attributes may be attributes characterizing the section for displaying the state of the driving gas or the section for displaying the state of the gas in the patient circuit, including but not limited to one or more of length, width, area, color saturation or display brightness.

It can be understood that in one embodiment the magnitude of the change in the volume of the driving gas may be related to the magnitude of the change in the indication attribute of the corresponding section for displaying the state of the driving gas. That is, the greater the change in the volume of the driving gas, the greater the change in the corresponding indication attribute. For example, if the indication attribute is length, as the volume of the driving gas gradually increases, the length of the section for displaying the state of the driving gas also gradually increases; if the indication attribute is color saturation, as the volume of the driving gas gradually decreases, the color saturation of the section for displaying the state of the driving gas also gradually decreases; and if the indication attribute is display brightness, as the volume of the gas in the patient circuit gradually increases, the display brightness of the section for displaying the state of the gas in the patient circuit also gradually increases. In the same way, the change in the volume of the gas in the patient circuit may be related to the indication attribute of the section for displaying the state of the gas in the patient circuit, which is the same as processing the volume of the driving gas and will not be described here again.

Further, the control module in one embodiment can also perform integral of the curve of the change in the volume of the driving gas and the curve of the change in the volume of the gas in the patient circuit, may calculate to obtain the corresponding volume of the driving gas and the volume of the gas in the patient circuit, and respectively set the specific absolute values of the indication attributes of the section for displaying the state of the driving gas and the section for displaying the state of the gas in the patient circuit as values proportional to the calculated volumes of the driving gas and the gas in the patient circuit. As such, when knowing the specific absolute values of the indication attributes of the section for displaying the state of the driving gas and the section for displaying the state of the gas in the patient circuit, the user can obtain the corresponding volumes of the driving gas and the gas in the patient circuit.

In order to make it more convenient for the user to know the volume of the driving gas and the volume of the gas in the patient circuit, the electronic display interface in one embodiment may also include a scale used for calibrating the volume of the driving gas and the volume of the gas in the patient circuit by measuring the specific numerical values of the above indicator parameter values. For example, when the parameter type of the above indicator parameter value is length, a scale used for calibrating the volume of the driving gas and the volume of the gas in the patient circuit by measuring the length can be provided in a lengthwise direction of the section for displaying the state of the driving gas and the section for displaying the state of the gas in the patient circuit.

Of course, since the ventilation state indicating graphic in one embodiment is not merely limited to a two-dimensional planar indicating graphic, and may also be a three-dimensional indicating graphic, the above indication attributes in one embodiment may include thickness or volume.

Further, the control module in one embodiment may be further used for, when abnormal ventilation is detected, indicating corresponding abnormal ventilation information on the ventilation state indicating graphic. Here, the abnormal ventilation includes one or more of ventilation failure of the anesthesia machine, patient disconnection, and insufficient gas supply of the anesthesia machine.

In one embodiment, the current anesthesia machine ventilation failure can be determined by detecting whether the current anesthesia machine is unable to perform ventilation, and if so, it can be determined that there is a ventilation failure. In addition, in one embodiment, a detection value of a flow sensor on a patient end can be used to determine whether there is patient disconnection, and if the detection value of the flow sensor on the patient end drops sharply or is zero, it can be determined that there is patient disconnection currently. Secondly, in one embodiment, it can be determined whether there is a problem of insufficient gas supply by determining whether the volume of fresh gas supply is less than the sum of consumption volume and leakage volume, and if so, it can be determined that gas supply of the current anesthesia machine is insufficient. Here, the consumption volume includes the consumption volume of the patient and/or the consumption volume of the $CO_2$ absorption tank; and the leakage volume includes the leakage volume of the system and/or the leakage volume of the patient end.

In one embodiment, specifically, the abnormal ventilation can be indicated by one or more of the indication attribute of the section for displaying the state of the driving gas, the indication attribute of the section for displaying the state of the gas in the patient circuit, and multimedia information. For example, when the patient disconnection occurs, the control module can control the indication attribute value of the section for displaying the state of a driving gas to become the maximum value, and control the indication attribute value of the section for displaying the state of the gas in the patient circuit to become the minimum value.

It can be understood that the above multimedia information includes, but is not limited to, one or more of an icon, a color, a text, or a sound used for indicating the abnormal ventilation.

In order to illustrate the ventilation state indication process of this disclosure more clearly, a ventilation state indicating graphic in the shape of a circular ring will be described below as an example. FIGS. 7a to 7d show indicating results of ventilation state indicating graphics of the anesthesia machine in different ventilation states.

Figure 7A:
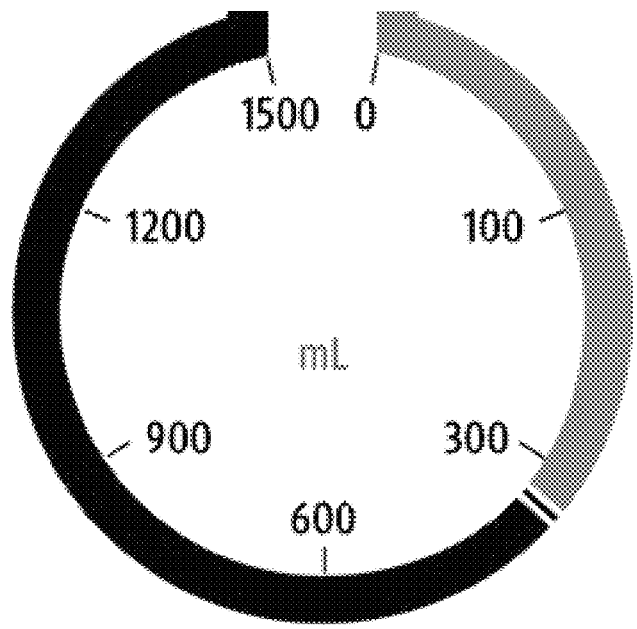
FIGS. 7a to 7b are indicating result diagrams of ventilation state indicating graphics of the anesthesia machine disclosed in an embodiment of this disclosure in different ventilation states.
Figure 7B:
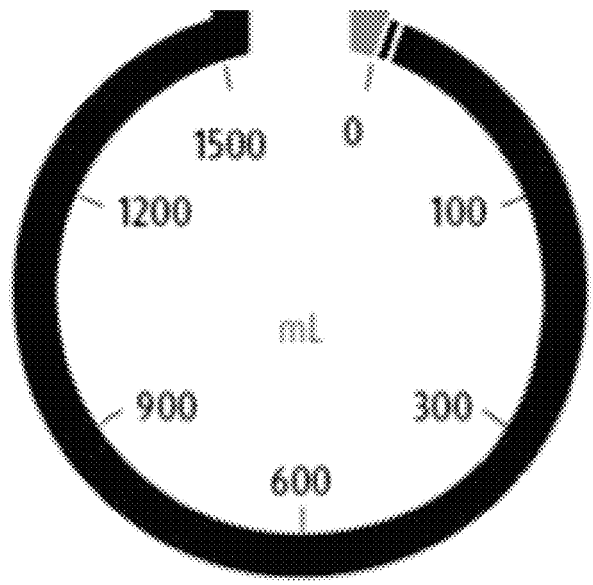
Figure 7C:
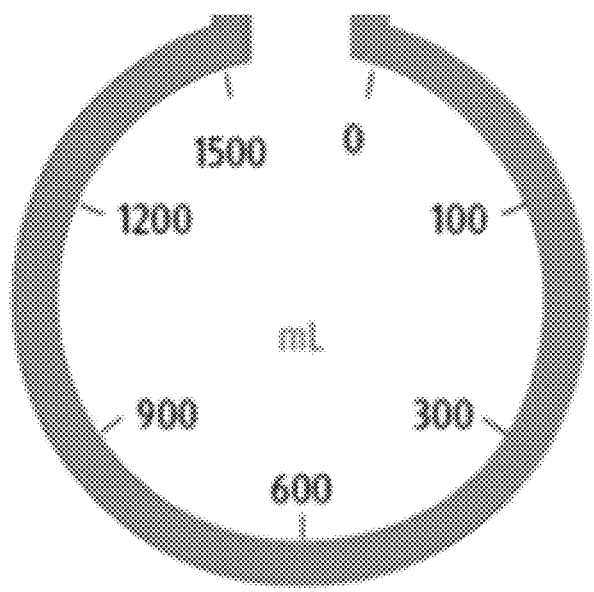
Figure 7D:
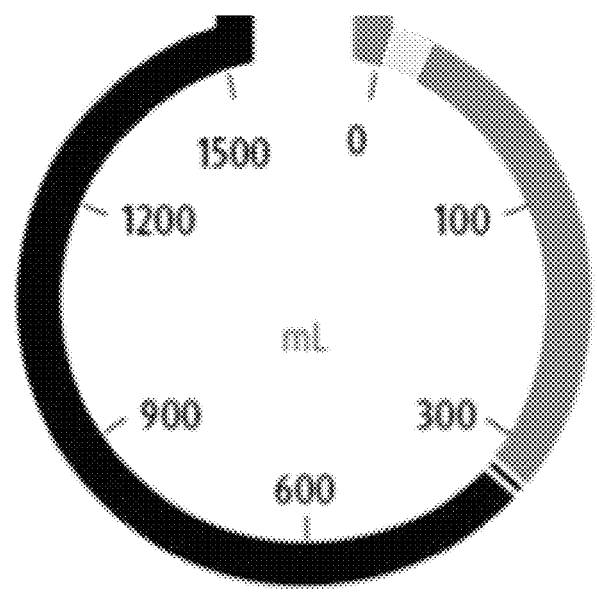

In FIG. 7a, different colors in the ventilation state indicating graphic may represent different gas components, a gray ring segment being the section for displaying the state of the driving gas, and a black ring segment being the section for displaying the state of the gas in the patient circuit. When the gray ring segment extends toward the black ring segment, it indicates that the patient is inhaling, and when the black ring segment extends toward the gray ring segment, it may indicate that the patient is exhaling. That is, in one embodiment, flow directions of different gases in the anesthesia machine are represented by the change in the length of the different ring segments. In FIG. 7b, when the mechanical ventilation fails and a ventilator stops, in the ventilation state indicating graphic, the length of the ring segment that was originally gray becomes zero, and the length of the ring segment no longer changes. In FIG. 7c, when the patient disconnection occurs, the entire ring of the ventilation state indicating graphic turns gray, and the length of the gray ring segment no longer changes. In FIG. 7d, when the fresh gas supply is insufficient, the ventilation state indicating graphic cannot return to the zero point, and a light gray abnormality identifier may be displayed near the zero scale of the ventilation state indicating graphic and is used for characterizing the current insufficient gas supply of fresh gas. Of course, in a specific implementation, two gases can also be distinguished by filling the corresponding portions representing the driving gas and the gas in the patient circuit with different patterns.

Further, the control module in one embodiment can also be used for acquiring the distance between an eye of a target observer and a display device. The indicating graphic display size that has a positive correlation with the distance is determined. According to the indicating graphic display size, the ventilation state indicating graphic may be correspondingly displayed in the display device.

In one embodiment, the control module can specifically use a distance sensor to acquire the distance between the eye of the target observer and the display device. The above distance sensor may include all sensors that can detect a distance, for example, various depth sensors.

In one embodiment, the larger the distance between the eye of the target observer and the display device, the larger the size of the ventilation state indicating graphic displayed in the display device, which makes it convenient for the target observer to clearly see the ventilation state of the anesthesia machine even when standing far away from the anesthesia machine.

In one embodiment, the above display device may include, but is not limited to, a wearable smart device and/or a hand-held smart device and/or a desktop computer.

Figure 8:
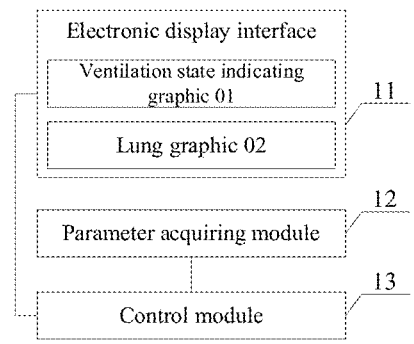
FIG. 8 is a structural diagram of a specific ventilation state indication system of an anesthesia machine disclosed in an embodiment of this disclosure.

As shown in FIG. 8, according to each of the foregoing embodiments, the embodiment of this disclosure further discloses a specific anesthesia machine ventilation state indication system, may include: an electronic display interface 11 may include one ventilation state indicating graphic 01 and one lung graphic 02; a parameter acquiring module 12 may be used for acquiring a ventilation parameter; and a control module 13 may be used for obtaining a change in the volume of the driving gas and a change in the volume of the gas in the patient circuit according to the ventilation parameter acquired by the parameter acquiring module 12, employing the ventilation state indicating graphic 01 to dynamically display at the same time the change in the volume of the driving gas and the change in the volume of the gas in the patient circuit on the electronic display interface 11, and indicating the change in the volume of the gas in the patient circuit according to the lung graphic 02.

Specifically, the above control module can be used for indicating the change in the volume of the gas in the patient circuit according to the change in a graphic parameter of the lung graphic and/or the change in an internal fill graphic of the lung graphic.

Here, the graphic parameter may include one or more of size, color, or brightness of the lung graph.

In one embodiment, when the patient is inhaling, any one or more of the size of the lung graph, the color saturation, the brightness, and the filling degree of the internal fill graphic on the lung graphic can gradually increase.

Further, the control module can be further used for, when abnormal ventilation is detected, indicating corresponding abnormal ventilation information on the lung graphic. For example, the purpose of indicating abnormal ventilation can be achieved by adding an abnormality identifier or adding a highlight text onto the lung graphic.

FIGS. 9a to 9d show indicating results of ventilation state indicating graphics and lung graphics of the anesthesia machine in different ventilation states.

Figure 9A:
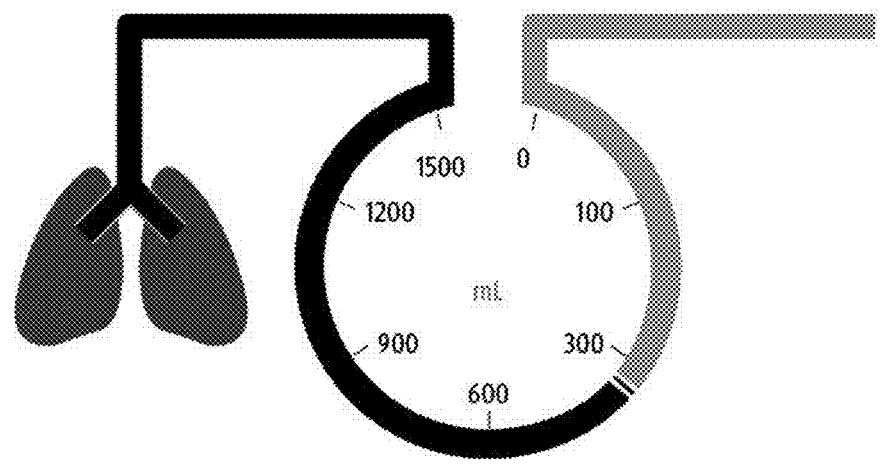
FIGS. 9a to 9d are indicating result diagrams of ventilation state indicating graphics and lung graphics of the anesthesia machine disclosed in an embodiment of this disclosure in different ventilation states.
Figure 9B:
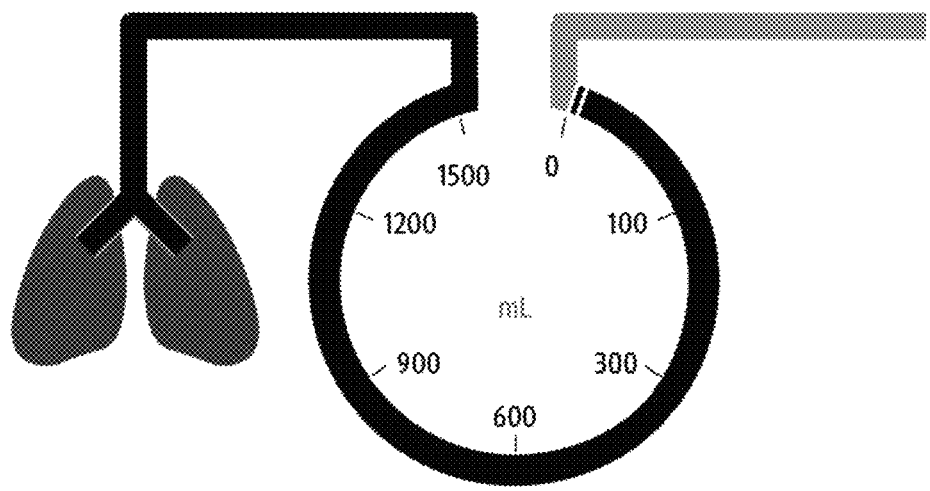
Figure 9C:
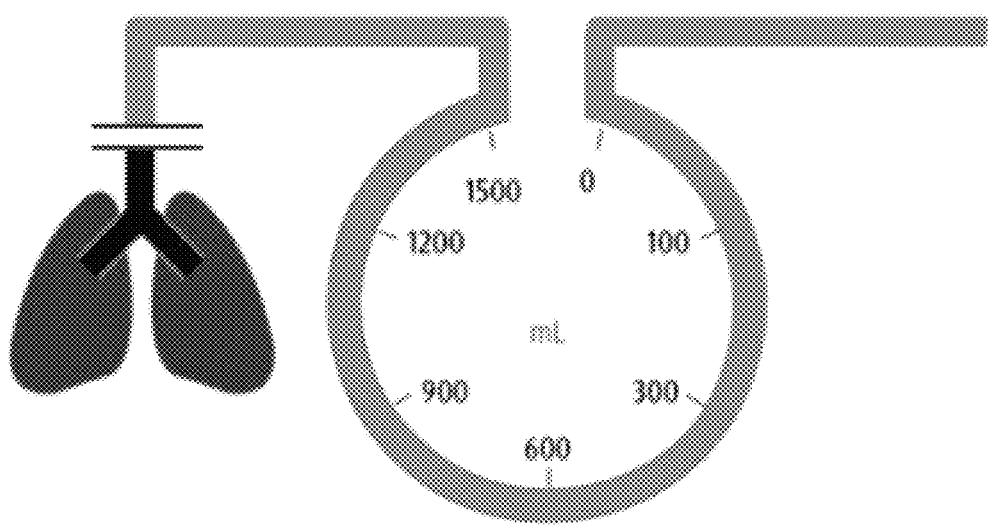
Figure 9D:
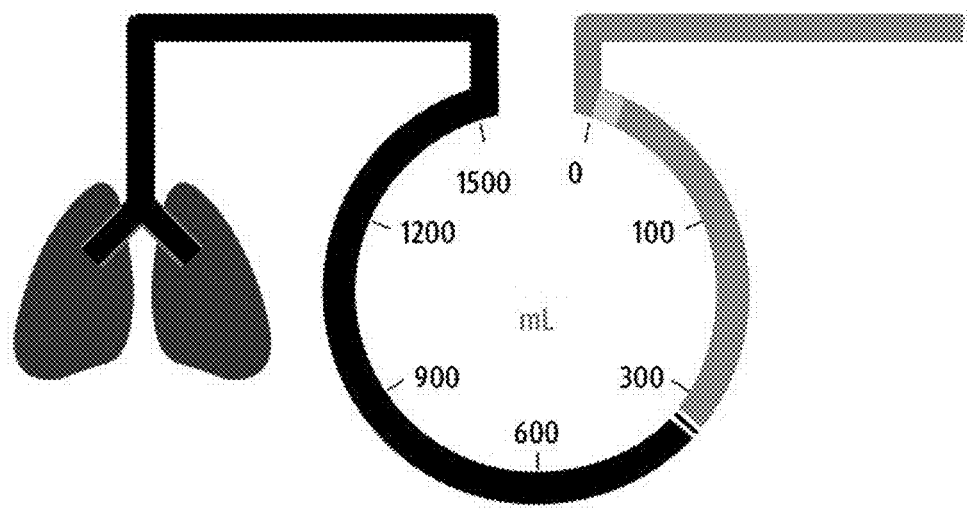

In FIG. 9a, different colors in the ventilation state indicating graphic represent different gas components, the gray ring segment represents the driving gas of the anesthesia machine, and the black ring segment represents the gas in the patient circuit. When the gray ring segment extends toward the black ring segment, it may indicate that the patient is inhaling, and when the black ring segment extends toward the gray ring segment, it may indicate that the patient is exhaling. That is, in one embodiment, flow directions of different gases in the anesthesia machine may be represented by the change in the length of the different ring segments. The change in the size of the lung graphic visually may indicate whether the patient is inhaling or exhaling. In addition, the volume of the current gas supply can be obtained according to the moving range of the position where the gray and black interface is located. In FIG. 9b, when the mechanical ventilation fails and a ventilator stops, in the ventilation state indicating graphic, the length of the ring segment that may be originally gray becomes zero, the length of the ring segment no longer changes, and the size of the lung graphic also no longer changes. In FIG. 9c, when the patient disconnection occurs, the entire ring of the ventilation state indicating graphic may turn gray, the length of the gray ring segment no longer changes, and the size of the lung graphic also no longer changes. In addition, a tube disconnection symbol can also be displayed at the connection between the ventilation state indicating graphic and the lung graphic to characterize the patient disconnection. In FIG. 9d, when the fresh gas supply is insufficient, the ventilation state indicating graphic cannot return to the zero point, and a light gray indicating zone may be displayed near the zero scale of the ventilation state indicating graphic and may be used for characterizing the current insufficient gas supply of fresh gas.

In addition, this disclosure further discloses an anesthesia machine may include the anesthesia machine ventilation state indication system disclosed in the foregoing embodiments, the anesthesia machine further may include a driving gas branch, a bellows-free gas exchanger, a patient circuit and a fresh gas branch.

It should be noted that the above bellows-free gas exchanger may be a device, different from a bellows, for isolating the driving gas from the gas in the patient circuit. Here, the above bellows-free gas exchanger may be specifically a volume reflector or a gas storage bag, etc.

Regarding the more specific configuration and working process of the above anesthesia machine ventilation state indication system, reference can be made to the corresponding contents disclosed in the foregoing embodiments and thus will not be described here again.

The embodiments in the description may be all described in a progressive manner, each of the embodiments focuses on the differences from the other embodiments, and reference may be made to each other for the same or similar parts among the embodiments. The apparatuses disclosed in the embodiments correspond to the methods disclosed in the embodiments and are thus described relatively simply, and reference may be made to the description of the methods for the related parts.

Those skilled in the art should be further aware that the unit and algorithm steps of the various examples described in conjunction with the embodiments disclosed herein can be implemented in electronic hardware, computer software, or a combination of both. In order to clearly illustrate hardware and software interchangeability, the compositions and steps of the various examples have been generally described in terms of function in the above description. Whether these functions are performed in hardware or software depends on the specific application and design constraints of the technical solution. Those skilled in the art could use different methods to implement the described functions for each particular application, but such implementation should not be considered to be beyond the scope of this disclosure.

The steps of the method or algorithm described in conjunction with the embodiments disclosed herein can be implemented with hardware, a software module executed by the control module, or a combination thereof. The software module can be disposed in a random access memory (RAM), a memory, a read-only memory (ROM), an electrically programmable ROM, an electrically erasable programmable ROM, a register, a hard disk, a removable disk, CD-ROM, or any other form of storage medium known in the art.

Finally, it should be noted that the terms of relationship herein, such as first and second, are used only to distinguish one entity or operation from another entity or operation, without necessarily requiring or implying any such actual relationship or sequence between these entities or operations. Moreover, the terms "comprise," "include" or any variation thereof are intended to cover a non-exclusive inclusion, so that a process, method, article or device that includes a series of elements not only includes those elements but also includes other elements not expressly listed or further includes elements inherent to such a process, method, article, or device. In the absence of more restrictions, the element defined by the phrase "including a/an . . . " does not exclude the presence of a further identical element in the process, method, article or device that includes the element.

An anesthesia machine and a ventilation state indication system thereof provided by this disclosure have been described in detail, the principle and implementation of this disclosure have been illustrated with reference to the specific examples, and the above description of the embodiments is merely for the purpose of assisting in understanding the method of this disclosure and its core concept. Moreover, for those skilled in the art, there can be modifications in the specific implementation and application scope based on the concept of this disclosure. To sum up, the content of this specification should not be construed as limiting this disclosure.

The invention claimed is:

1. An anesthesia machine ventilation state indication system that indicates a ventilation state of an anesthesia machine, the system comprising:
   an electronic display interface that comprises a ventilation state indication graphic;
   a parameter acquiring module that acquires a ventilation parameter; and
   a controller that obtains a change in a volume of a driving gas and a change in a volume of a gas in the patient circuit according to the ventilation parameter acquired, and employs the ventilation state indication graphic to dynamically and simultaneously display the change in the volume of the driving gas and the change in the volume of the gas in the patient circuit on the electronic display interface,
   wherein the ventilation state indication graphic is a circular ring comprising two ring segments respectively representing the gas in the patient circuit and the driving gas, and a gap between the two ring segments, wherein changes in lengths the two ring segments indicate the ventilation state of the anesthesia machine.

2. The anesthesia machine ventilation state indication system of claim 1, wherein the parameter acquiring module comprises an expiratory flow sensor that acquires an expiratory flow, and an inspiratory flow sensor that acquires an inspiratory flow or a driving gas flow sensor that acquires a driving gas flow; and the controller calculates the change in the volume of the gas in the patient circuit according to the expiratory flow acquired, and calculates the change in the volume of the driving gas according to the inspiratory flow or the driving gas flow acquired.

3. The anesthesia machine ventilation state indication system of claim 1, wherein the controller respectively controls a change in an indication attributes of the section for displaying the state of the driving gas and a change in an indication attribute of the section for displaying the state of the gas in the patient circuit according to the change in the volume of the driving gas and the change in the volume of the gas in the patient circuit; and wherein the indication attributes comprise one or more of length, width, area, thickness, volume, color saturation, and display brightness.

4. The anesthesia machine ventilation state indication system of claim 1, wherein the controller further, when an abnormal ventilation is detected, indicates corresponding abnormal ventilation information on the ventilation state indication graphic.

5. The anesthesia machine ventilation state indication system of claim 4, wherein the abnormal ventilation comprises one or more of ventilation failure of the anesthesia machine, patient disconnection, and insufficient gas supply of the anesthesia machine.

6. The anesthesia machine ventilation state indication system of claim 4, wherein the abnormal ventilation is indicated by one or more of the indication attribute of the section for displaying the state of the driving gas, the indication attribute of the section for displaying the state of the gas in the patient circuit, and multimedia information.

7. The anesthesia machine ventilation state indication system of claim 6, wherein the multimedia information comprises one or more of an icon, a color, a text, and a sound for indicating the abnormal ventilation.

8. The anesthesia machine ventilation state indication system of claim 1, wherein the electronic display interface further comprises a lung graphic, through which the controller indicates the change in the volume of the gas in the patient circuit.

9. The anesthesia machine ventilation state indication system of claim 8, wherein the controller is used for indicating the change in the volume of the gas in the patient circuit according to through at least one of a change in a graphic parameter of the lung graphic and a change in an internal fill graphic of the lung graphic; and wherein the graphic parameter comprises one or more of size, color, or brightness of the lung graphic.

10. The anesthesia machine ventilation state indication system of claim 8, wherein the controller further, when an abnormal ventilation is detected, indicates corresponding abnormal ventilation information on the lung graphic.

11. An anesthesia machine comprising an anesthesia machine ventilation state indication system that indicates a ventilation state of the anesthesia machine, the anesthesia machine ventilation state indication system comprising:
- an electronic display interface that comprises a ventilation state indication graphic;
- a parameter acquiring module that acquires a ventilation parameter; and
- a controller that obtains a change in a volume of a driving gas and a change in a volume of a gas in the patient circuit according to the ventilation parameter acquired, and employs the ventilation state indication graphic to dynamically and simultaneously display the change in the volume of the driving gas and the change in the volume of the gas in the patient circuit on the electronic display interface, wherein the ventilation state indication graphic is a circular ring comprising two ring segments respectively representing the gas in the patient circuit and the driving gas, and a gap between the two ring segments, wherein changes in lengths of the two ring segments indicate the ventilation state of the anesthesia machine,
wherein the anesthesia machine further comprises a driving gas branch, a bellows-free gas exchanger, a patient circuit, a fresh gas branch and a patient circuit.

12. The anesthesia machine of claim 11, wherein the ventilation state indication graphic comprises a section for displaying a state of a driving gas and a section for displaying a state of a gas in the patient circuit.

13. The anesthesia machine of claim 12, wherein the controller further, when an abnormal ventilation is detected, indicates corresponding abnormal ventilation information on the ventilation state indication graphic.

14. The anesthesia machine of claim 13, wherein the abnormal ventilation comprises one or more of ventilation failure of the anesthesia machine, patient disconnection, and insufficient gas supply of the anesthesia machine.

15. The anesthesia machine of claim 13, wherein the abnormal ventilation is indicated by one or more of the indication attribute of the section for displaying the state of the driving gas, the indication attribute of the section for displaying the state of the gas in the patient circuit, and multimedia information.

16. The anesthesia machine of claim 13, wherein the electronic display interface further comprises a lung graphic, through which the controller indicates the change in the volume of the gas in the patient circuit.

17. The anesthesia machine of claim 16, wherein the controller is used for indicating the change in the volume of the gas in the patient circuit according to through at least one of a change in a graphic parameter of the lung graphic and a change in an internal fill graphic of the lung graphic; and wherein the graphic parameter comprises one or more of size, color, or brightness of the lung graphic.

18. The anesthesia machine of claim 16, wherein the controller further, when an abnormal ventilation is detected, indicates corresponding abnormal ventilation information on the lung graphic.

19. The anesthesia machine ventilation state indication system of claim 4, wherein
when the abnormal ventilation is the ventilation failure of the anesthesia machine, the length of the ring segment representing the driving gas becomes zero, and the length of the ring segment representing the gas in the patient circuit no longer changes so as to indicate the ventilation failure in the anesthesia machine;
when the abnormal ventilation is the tube disconnection, the length of the ring segment representing the gas in the patient circuit becomes zero, and the length of the ring segment representing the driving gas no longer changes so as to indicate the tube disconnection.

20. The anesthesia machine ventilation state indication system of claim 8, wherein when the abnormal ventilation is the tube disconnection characterizing patient disconnection from the anesthesia machine, a tube disconnection symbol is further displayed at a connection between the ventilation state indicating graphic and the lung graphic to characterize the patient disconnection.

* * * * *